United States Patent
Einarsson et al.

(10) Patent No.: US 6,592,539 B1
(45) Date of Patent: Jul. 15, 2003

(54) ORTHOTIC OR PROSTHETIC SLEEVE FORMED OF ELASTICIZED FABRIC SECTIONS HAVING DIFFERENT ELASTIC STIFFNESS

(75) Inventors: Palmi Einarsson, Kópavogur (IS); Sigurdur Á. Ásgeirsson, Kópavogur (IS); Hilmar Br. Janusson, Seltjarnarnes (IS)

(73) Assignee: Ossur HF, Rujavik (GB)

( * ) Notice: Subject to any disclaimer, the term of this patent is extended or adjusted under 35 U.S.C. 154(b) by 0 days.

(21) Appl. No.: 09/516,221

(22) Filed: Mar. 1, 2000

Related U.S. Application Data
(60) Provisional application No. 60/122,320, filed on Mar. 1, 1999.

(51) Int. Cl.⁷ .............. A61F 13/00; A61F 5/00; A61F 2/78
(52) U.S. Cl. .............. 602/62; 602/63; 602/26; 623/32
(58) Field of Search .............. 602/23, 20, 26, 602/60–63, 75–76; 623/32–36; 2/239–242; 66/178 R, 172 E

(56) References Cited

U.S. PATENT DOCUMENTS

| | | | |
|---|---|---|---|
| 663,749 A | 12/1900 | Gorse | |
| 940,585 A * | 11/1909 | Drennan | 2/239 |
| 967,585 A * | 8/1910 | Teufel | 2/239 |
| 1,544,641 A * | 7/1925 | Guinzburg | 2/239 |
| 1,890,299 A * | 12/1932 | Mutchler | 2/239 |
| 2,169,203 A * | 8/1939 | Hinchliff | 2/239 |
| 2,255,224 A * | 9/1941 | Luhn | 2/239 |
| 2,268,751 A * | 1/1942 | Harris | 2/239 |
| 3,789,842 A * | 2/1974 | Froimson | 602/75 |
| 4,027,667 A * | 6/1977 | Swallow | 2/239 |
| 4,172,456 A * | 10/1979 | Zens | 2/240 |
| 4,479,272 A | 10/1984 | Beldzisky | |
| 4,822,371 A * | 4/1989 | Jolley et al. | 623/32 |
| 4,908,037 A | 3/1990 | Ross | 623/32 |
| 5,007,418 A | 4/1991 | Bartizal et al. | |
| 5,133,199 A | 7/1992 | Parikh et al. | |
| 5,367,708 A | 11/1994 | Fujimoto | |
| 5,382,223 A * | 1/1995 | Springs | 602/6 |
| 5,419,161 A | 5/1995 | Bodenschatz et al. | |
| 5,507,834 A * | 4/1996 | Laghi | 623/36 |
| 5,588,956 A | 12/1996 | Billotti | |
| 5,593,454 A | 1/1997 | Helmy | 623/32 |
| 5,830,237 A | 11/1998 | Kania | 623/37 |
| 5,865,776 A * | 2/1999 | Springs | 602/26 |
| 5,897,517 A | 4/1999 | Laghi | |
| 6,092,397 A * | 7/2000 | Cortinovis | 66/184 |
| 6,136,039 A * | 10/2000 | Kristinsson et al. | 623/36 |
| 6,139,929 A * | 10/2000 | Hayton | 2/239 |
| 6,149,690 A * | 11/2000 | Belzidsky | 623/32 |

FOREIGN PATENT DOCUMENTS

| | | |
|---|---|---|
| EP | 0 498 062 A1 | 8/1992 |
| EP | 0 835 645 A1 | 4/1998 |

* cited by examiner

*Primary Examiner*—Denise M. Pothier
(74) *Attorney, Agent, or Firm*—Bacon & Thomas, PLLC

(57) ABSTRACT

An orthotic or prosthetic sleeve includes at least two elasticized fabric elements having different elastic stiffnesses in orthogonal directions connected together to form a tubular sleeve such that the direction of higher stiffness of one fabric element extends parallel with the sleeve axis and the direction of higher stiffness of the other element extends generally transversely of the sleeve axis. A three piece tubular sleeve may be arranged so that the middle section has a direction of higher stiffness extending transversely of the sleeve axis, with the end sections having the higher stiffness direction extending parallel with the sleeve axis.

6 Claims, 3 Drawing Sheets

ORTHOTIC OR PROSTHETIC SLEEVE FORMED OF ELASTICIZED FABRIC SECTIONS HAVING DIFFERENT ELASTIC STIFFNESS

This application claims the benefit of Provisional Application Ser. No. 60/122,320 filed Mar. 1, 1999.

BACKGROUND OF THE INVENTION

1. Field of the Invention

This invention relates to an elasticized sleeve construction suitable for orthotic and prosthetic applications.

2. Related Art

Orthotic and prosthetic elasticized sleeves are described in U.S. Pat. Nos. 4,908,037 and 5,830,237. Such sleeves are fabricated of elastic or elasticized materials and may be used to support and reinforce muscles, joints and extremities of those in need of such assistance and to provide an airtight seal between a residual limb of an amputee and an prosthesis socket worn by the amputee.

BRIEF SUMMARY OF THE INVENTION

An orthotic or prosthetic sleeve is formed by joining sections of elasticized fabric shaped in tubular form and joined at their axial ends to form a tubular sleeve extending in an axial direction. The sleeve may be cylindrical or may be curved.

In accordance with one embodiment of the invention, the elasticized fabric used to make the sleeve sections exhibits different elastic stiffness (different elasticity) in the lengthwise and widthwise directions of the fabric. That is, the fabric is elastically stiffer (has less elasticity or a higher modulus of elasticity) in one direction than in a direction perpendicular to the one direction.

By joining together the fabric sections in a specified configuration, the sleeve will have at least one section having its direction of higher elastic stiffness in a direction transversely of the sleeve and at least one section having its direction of higher elastic stiffness extending along the axial direction of the sleeve.

Other stiffening elements may be provided along the length of the sleeve in accordance with known principles to provide lateral rigidity to the sleeve.

The entire inner surface of the sleeve is coated with a discrete layer of silicone elastomer that is firmly bonded to the fabric material constituting the sleeve. The silicone elastomer layer is thick enough and soft enough to be very comfortable to the user and to provide an airtight seal between the sleeve and the skin.

In a preferred embodiment, at least two elasticized fabric elements are connected together to define a tubular sleeve extending on an axis and having at least two fabric sections. The elasticized fabric constituting these sections has a higher elastic stiffness along one direction of the fabric than along an orthogonal direction relative to the said one direction. One of the at least two sections is formed so that the direction of higher stiffness of the fabric extends axially along the sleeve axis and the other section is formed so that the direction of higher stiffness extends generally transversely of the sleeve axis.

In accordance with one embodiment of the invention, at least three elasticized fabric elements are utilized to define the orthotic or prosthetic sleeve of the invention, wherein the elements are fabricated in tubular form and connected along their axial ends to define a tubular sleeve having two end sections and a middle section.

The end sections are formed so that the direction of higher elastic stiffness of the fabric extends axially along the sections and the middle section is formed so that the direction of higher elastic stiffness of the fabric extends generally transversely of the sleeve axis.

The interior surface of the sleeve is entirely coated with a continuous, cured silicone elastomer material that forms a discrete layer on the inside surface of the sleeve.

The silicon elastomer preferably has a Shore 00 of 25–70; a minimum tensile strength of 230 lbs/inch; a 100% modulus of 8 psi; a 500% modulus of 61 psi; a minimum tear strength of 49 lbs/inch; a maximum tensile strength of 500 lbs/inch; and an elongation of about 1000%.

The tubular sleeve in accordance with one embodiment may be provided with a curvature along a portion of its length and wherein the section having its direction of higher stiffness extending generally transversely of the sleeve axis is located along the curvature.

In a preferred embodiment, stiffening ribs are provided extending lengthwise of the sleeve on diametrically opposite sides thereof, the stiffening ribs being formed of relative inelastic material, for example a relatively inelastic fabric.

A more detailed description of preferred embodiments of the invention is provided below and illustrated in the accompanying drawings.

DESCRIPTION OF THE DRAWINGS

With reference to the appended drawings:

FIG. 5 is a section view taken along line V—V of FIG. 1;

FIG. 6 is a section view taken along line VI—VI of FIG. 1;

DETAILED DESCRIPTION OF PREFERRED EMBODIMENTS OF THE INVENTION

Figure 1:
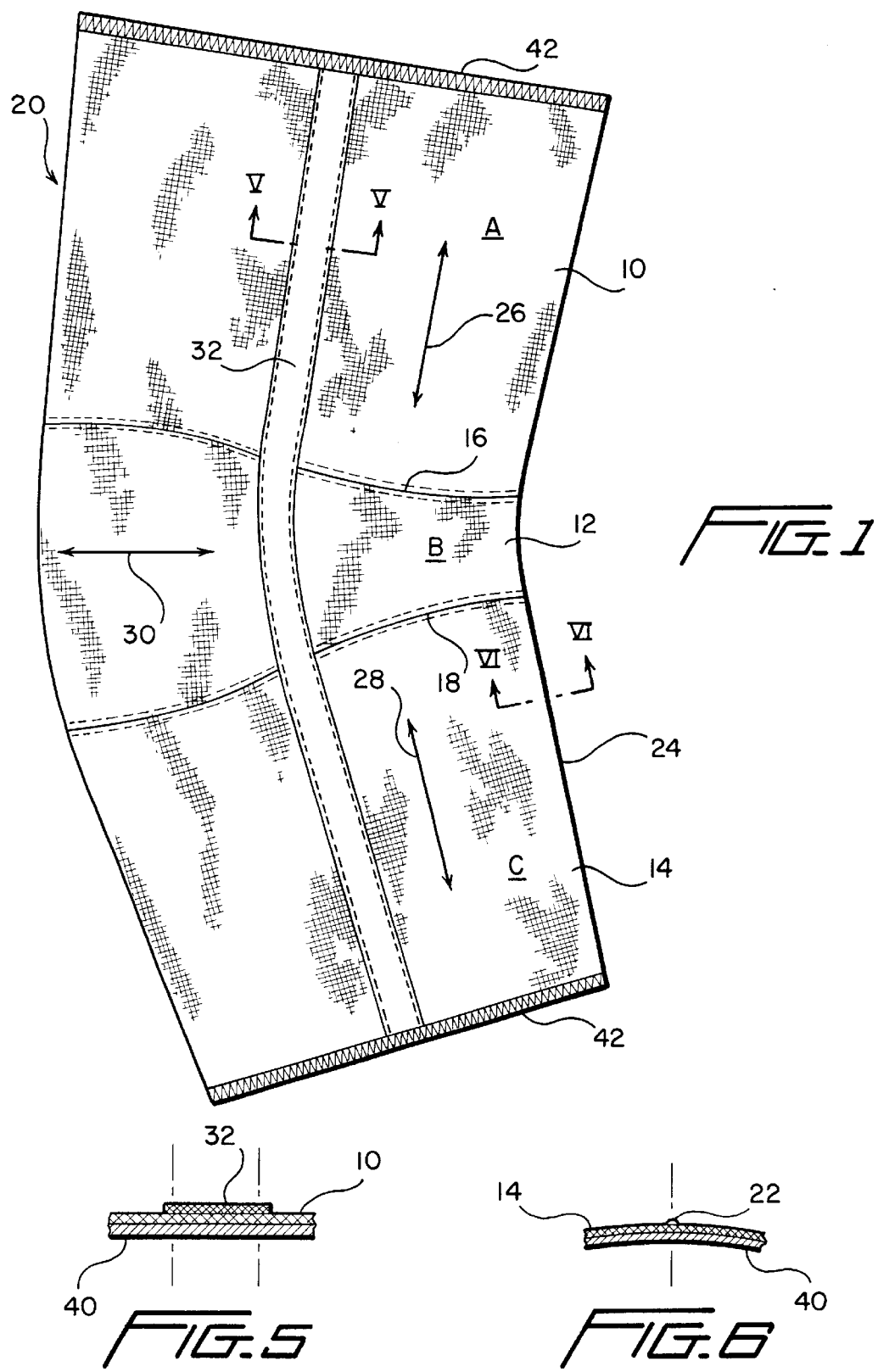
FIG. 1 is a side elevation view of one embodiment of an orthotic or prosthetic sleeve embodying the invention.
Figure 2:
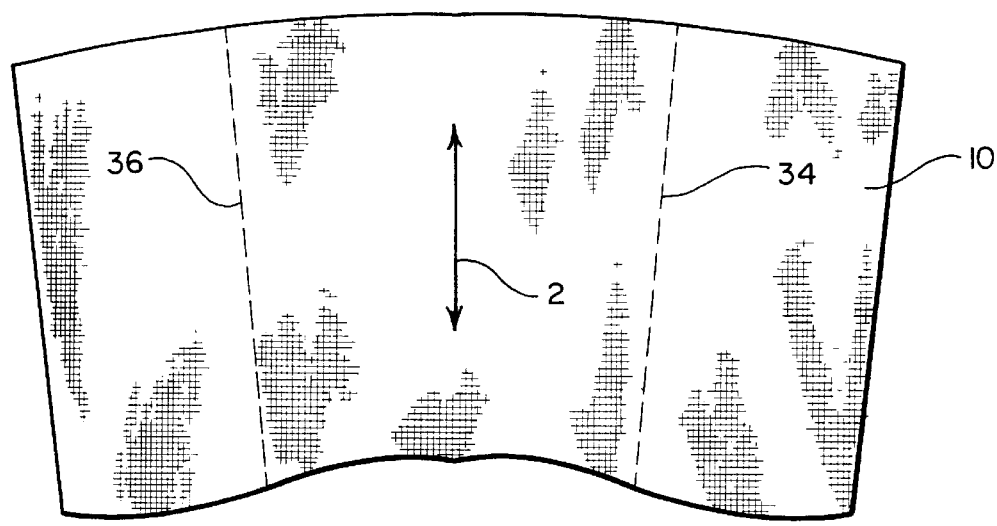
FIG. 2 is a plan view of a pattern suitable to make one section of the sleeve shown in FIG. 1.
Figure 3:
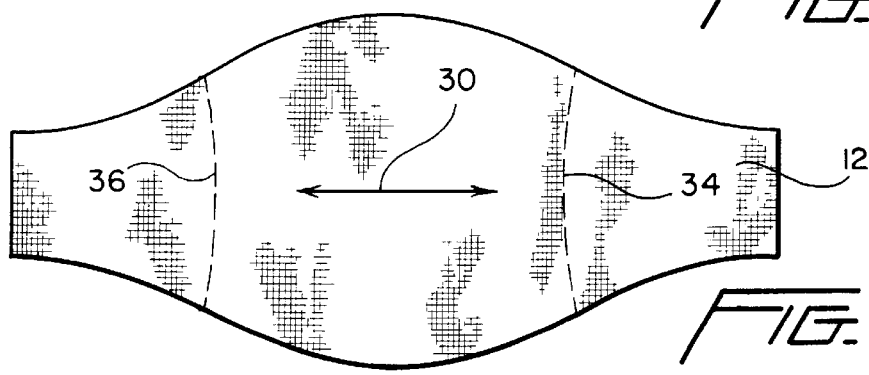
FIG. 3 is a plan view of a pattern suitable to make another section of the sleeve shown in FIG. 1.
Figure 4:
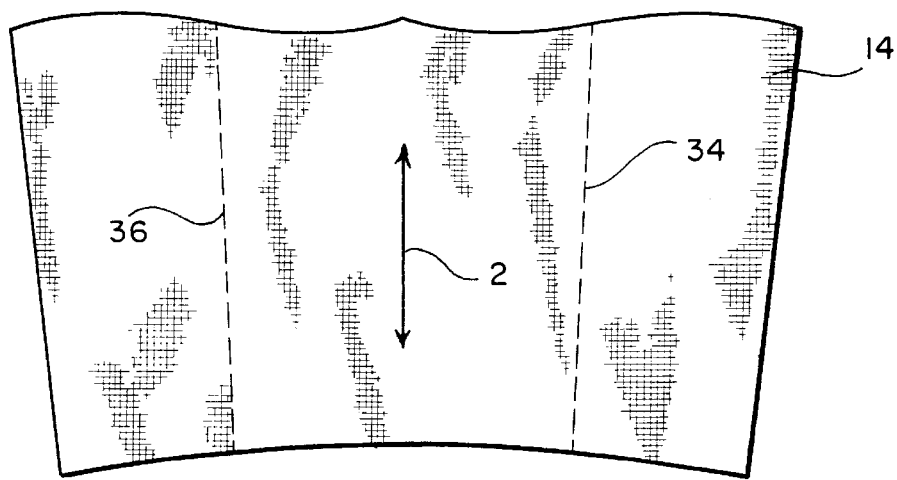
FIG. 4 is a pattern suitable to make another section of the sleeve shown in FIG. 1.

With reference to FIGS. 1–4, sections of elasticized fabric 10, 12 and 14 are cut along the patterns illustrated in FIGS. 2–4 and are then curved and sewn into tubular sections as shown in FIG. 1 to form axially extending cylindrical sections A, B and C, respectively, that are sewn together along stitching lines 16, 18 at their axial ends to form an axially extending tubular orthotic or prosthetic sleeve 20 that will be contoured in a relaxed state as illustrated in FIG. 1.

The individual sections 10, 12 and 14 each may be sewn along a lengthwise seam 22 along one side 24 of each section A, B or C of the sleeve 20 to form the individual tubular sections A, B and C.

The fabric used to make the sections 10, 12 and 14 is selected from any suitable porous, woven or non-woven tough, wear resistant elasticized fabric material that has elastic properties enabling the fabric to stretch within its elastic range in at least two orthogonal directions which, for the sake of convenience, may be referred to as lengthwise and widthwise of the fabric sections. One example of such an elasticized fabric is a material marketed under the name WEARFORCE™ by E. I. Dupont de Nemours.

In accordance with the invention, an elasticized fabric section 10 having a higher elastic stiffness (i.e., has less elasticity) in the axial direction of the sleeve (as depicted by arrows 26 in FIGS. 1 and 2) as compared with the elastic stiffness (elasticity) of the section in a direction transversely of the sleeve is used to make one sleeve section A and likewise the fabric section 14 used to make section C of sleeve 20 possess higher elastic stiffness in the axial direction of the sleeve as shown by arrow 28 in FIG. 1 as compared with the elastic stiffness of the section transversely of the sleeve.

That is, elasticized fabric sections 10 and 14 exhibit higher elastic stiffness (i.e., have less elasticity) in the longitudinal or axial direction of the fabric sections when they are made up into the sleeve sections A and C relative to the elastic stiffness of the sections in a direction essentially transversely of or orthogonal to the directions depicted by arrows 26. If the fabric constituting sections 10 and 14 are made of woven yarns, for example, typically the sections will have a higher elastic stiffness (less elasticity) along the "length" of the fabric in the direction of the warp yarns as compared with the elastic stiffness in the transverse "widthwise" direction corresponding to the direction of the fill or weft yarns.

On the other hand, any suitable porous, woven or non-woven fabrics including textiles that possess different elastic stiffness properties in perpendicular or orthogonal directions can be used to form the sleeve of the invention.

Middle fabric section 12 is cut from an elasticized fabric in accordance with the pattern shown in FIG. 3 so that the direction of higher elastic stiffness of the fabric section 12 extends along the direction depicted by arrow 30. When shaped and stitched to form the middle section B of the sleeve 20 as shown in FIG. 1, the direction of higher stiffness of the fabric section 12 will extend generally transversely of the axial direction of the sleeve 20. It will be apparent that the direction of higher stiffness shown by arrow 30 is generally perpendicular to the direction of higher stiffness depicted by arrows 26 and 28 associated with sleeve sections A and C. If a curvature is formed in the sleeve 20 as shown in FIG. 1, the direction depicted by arrow 30 may not be precisely perpendicular to the directions depicted by arrows 26 and 28 and likewise the directions depicted by arrows 26 and 28 may not extend in parallel or collinear directions. However, the intended result of providing differential elastic stiffness properties to the sleeve 20 will be obtained provided that the principal direction of higher elastic stiffness of the fabrics 10 and 14 extend generally along directions that correspond to the general axial direction of the sleeve section formed by the sections and if the principal direction of higher elastic stiffness of the fabric section 12 extends generally transversely of the axis of the sleeve section formed by the fabric 12.

A stiffening rib 32 preferably formed from a relatively inelastic woven or non-woven fabric is sewn along one side of the sleeve 20 in the axial direction thereof and a similar stiffening rib (not shown) is stitched along the opposite side of the sleeve 20 in a direction parallel with the rib 32. Each stiffening rib 32 preferably is continuously attached to the sleeve 20 along its length by a suitable connection which may include adhesive, stitching, or other connecting arrangements that will firmly secure the rib 32 continuously along the side of the sleeve 20.

To assist in the fabrication of the sleeve 20, and in particular to provide a guide for sewing the rib 32 to the sleeve sections A, B and C, each section may be provided with visible indicia in the form of guide lines 34, 36 that will be visible to a sewing machine operator or other assembly worker when the sections 10, 12 and 14 are curved into tubular sections and stitched or connected together, and that can be used to guide the placement of the stiffening rib 32 onto the side of the sleeve 20 where it will be firmly secured to the sections A, B and C as shown for example in FIG. 1.

FIG. 5 is a cross section view taken along section line V—V showing rib 32 stitched to the outer surface of fabric section 10.

After the sleeve 20 has been fabricated in the manner described above by joining sections A, B and C, the inside surface of the entire sleeve is coated with a cured silicone elastomer (40) material that is firmly bonded as a discrete layer with the interior surface of the fabric sections 10, 12 and 14. The silicone elastomer material on the inside surface of the sleeve 20 is shown in FIGS. 5 and 6.

The cured silicone elastomer material may be applied by coating, film casting, injection molding or any other suitable process that will produce an air and moisture impermeable discrete elastomeric coating on the inside surface only of the sleeve 20 to provide an airtight sleeve that may be used in prosthetic applications as a seal between a residual limb and the proximal end of a prosthetic socket, particularly a below-the-knee (BTK) socket used to connect a residual limb with a prosthesis (e.g., a leg and foot).

When used in an orthotic application, the silicone elastomer coating optionally may be omitted to provide a flexible elasticized sleeve having differential elastic stiffness properties in the axial and transverse directions.

Figure 9:
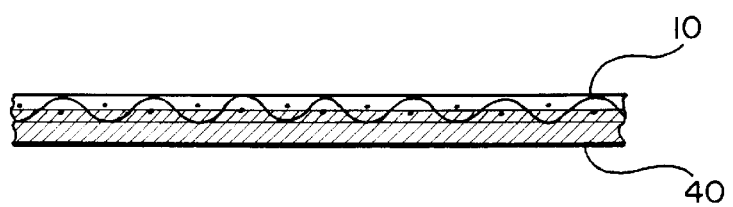
FIG. 9 is a representative section view through a portion of an orthotic or prosthetic sleeve embodying the invention showing a lamination of an outer porous fabric and an inner discrete layer of cured silicone elastomer material.

Preferably, the fabric used to make sections 10, 12 and 14 is porous and a cured silicone elastomer material 40 is partially impregnated into the porous structure of the fabric as shown, for example, in FIG. 9 where fabric section 10 is provided with a cured silicone elastomer material 40 on its inner side with the elastomer material forming a discrete layer partially impregnated into the porous structure of the fabric 10.

It will be evident that when the silicone elastomer material 40 is bonded with the fabric 10, the elastic properties of the combined laminated material will reflect the composite elastic properties of the elasticized fabric 10 and the elastomer material 40. That is, the composite laminate will exhibit higher elastic stiffness (less elasticity) in one direction than in an orthogonal direction but the degree of elasticity normally exhibited by the elasticized fabric will be modulated to some extent by the elasticity of the silicone material.

If the sleeve 20 is to include a curvature as illustrated in FIG. 1, the curvature can be established by the shapes of the fabric pattern sections 10, 12 and 14 and the curvature can be reinforced by application and/or curing of the silicone elastomer material 40 while it is being bonded to the fabric of the sleeve and while the fabric is in its final desired sleeve configuration, including its curvature.

If desired, the fabric sections of the sleeve 20 may be elastically distended in a desired direction or curvature while the silicone elastomer is bonded thereto and cured to provide a permanent set to the fabric of any of the sections A, B or C or of the entire sleeve in such distended configuration.

Figures 7, 8:
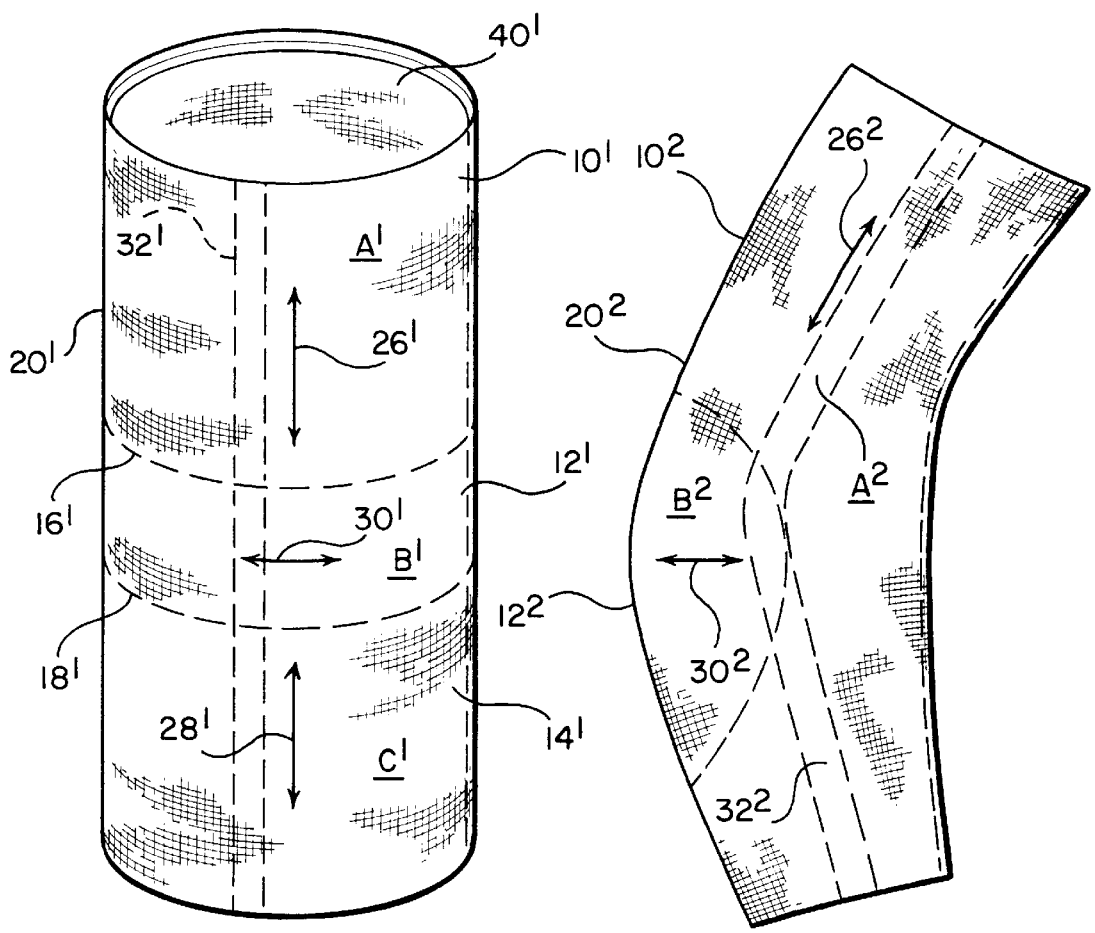
FIG. 7 shows another embodiment of an orthotic or prosthetic sleeve embodying the invention.
FIG. 8 is another embodiment of an orthotic or prosthetic sleeve embodying the invention.

The sleeve 20 may be formed without a curvature as shown in FIG. 7 which illustrates another embodiment of the invention. In accordance with FIG. 7, fabric sections $10^1$, $12^1$ and $14^1$, may be rolled and sewn and otherwise joined together to form sleeve section $A^1$, $B^1$ and $C^1$. Tubular sleeve sections $A^1$, $B^1$ and $C^1$ are joined by stitching or otherwise connected smoothly along their axial ends as shown at $16^1$, $18^1$ to form a cylindrical orthotic or prosthetic sleeve $20^1$. This embodiment of the orthotic or prosthetic $20^1$ is fabricated using fabric sections $10^1$ and $14^1$ that correspond to fabric sections 10 and 14 of FIGS. 2 and 4, that is, the fabric of sections $10^1$ and $14^1$ both exhibit higher elastic stiffness in the direction of arrows $26^1$ and $28^1$ (lengthwise of the fabric) than in a direction generally perpendicular to the direction of said arrows (widthwise of the fabric). When fabricated into the sleeve sections $A^1$ and $C^1$, the direction of higher elastic stiffness of the fabric in each section extends along the directions of arrows $26^1$ and $28^1$ as shown in FIG. 7.

In a similar manner, the fabric section $12^1$ when fabricated into the middle section $B^1$ of orthotic of prosthetic sleeve $20^1$ exhibits higher elastic stiffness in the direction of arrow $30^1$ that extends generally transversely of the axial direction of sleeve $20^1$.

Sleeve $20^1$ may be entirely coated on its interior surface with a discrete layer of cured silicone elastomer material $40^1$ in the same manner as described previously in regard to the embodiment of the sleeve 20 shown in FIG. 1. If desired, the sleeve 201 may be deformed out of a purely straight cylindrical form into any desired shape or configuration by thermal or other setting procedures applied to the fabric or by coating and curing the silicone elastomer material on one side (the inside) of the fabric sections $10^1$, $12^1$ and $14^1$ with the fabric distended or curved in a desired configuration so that the fabric and silicone elastomer composite takes a permanent set in accordance with the curvature established during the silicone elastomer coating and curing procedure.

Optionally, a stiffening rib $30^1$ may be utilized on opposite sides of the sleeve $20^1$, such reinforcing rib $32^1$ being secured to the outer surface of the sleeve $20^1$ in a manner similar to the rib 32 described previously in connection with the embodiment shown in FIG. 1.

Another embodiment of the invention is shown in FIG. 8 where an orthotic or prosthetic sleeve $20^2$ is illustrated. In accordance with the embodiment shown in FIG. 8, the sleeve $20^2$ is formed of two sections of elasticized fabric that have been cut and seamed into a first tubular section $10^{2\ and}$ a second tubular section $12^2$. The sections $10^1$ and $12^2$ are cut from patterns that can be joined along their edges to form a generally elongated cylindrical sleeve $20^2$ having sections $A^2$ made of fabric section $10^2$ and section $B^2$ made of fabric $12^2$, the fabric sections being joined by stitching or other suitable joining procedures to form, for example, a curved sleeve $20^2$ from sections $A^2$ and $B^2$. Each fabric section has different elastic stiffness in generally perpendicular directions.

The sleeve section $A^2$ is made from a fabric having its higher elastic stiffness extending in the direction of arrow $26^2$ that extends generally lengthwise of the sleeve $20^2$ and the section $B^2$ is made of a fabric having its higher elastic stiffness direction extending as shown by arrow $30^2$, that is, generally transversely with respect to the longitudinal direction of sleeve $20^2$.

If desired, a relatively inelastic stiffening rib $32^2$ may optionally be applied to the diametrically opposed sides of the sleeve $20^2$ in the same manner as described previously in connection with sleeve 20 shown in FIG. 1.

The sleeve $20^2$ like the sleeves of the embodiments of the invention described previously may be entirely coated on its interior surface with a cured silicone elastomer material (not shown) that corresponds with the discrete coating or layer of elastomer material 40 described previously with regard to the embodiment of the invention shown in FIG. 1.

The silicone elastomer material 40 preferably has a Shore 00 of 25–70; a minimum tensile strength of 230 lbs/inch; a 100% modulus of 8 psi; a 500% modulus of 61 psi; a minimum tear strength of 49 lbs/inch; a maximum tensile strength of 500 lbs/inch; and an elongation of about 1000%.

The silicone elastomer material 40 used in the orthotic or prosthetic sleeves described above may be of uniform thickness in both circumferential and longitudinal directions or may have a varying thickness to accommodate varying anatomical shapes, protrusions, contours, etc. Various relief pads may be provided within the bodies of the sleeve embodiments described above to provide specific relief from localized pressure that may result from installation of the sleeve on a human limb or residual limb.

An overlock stitching 42 may be used at opposed ends of the sleeve (FIG. 1) to overlap and cover both fabric and silicone coating material to facilitate rolling up the sleeve, to provide an attractive appearance, and to reinforce and enhance the sealing ability of the sleeve at its ends.

In use, the sleeves described herein may be donned over a limb by a well known unrolling technique from a rolled up configuration if utilized for orthotic purposes to reinforce muscles and joints along desired directions of support. For example, the sleeves may be used in a knee or elbow area of a limb to provide stiffer support transversely of the knee or elbow joint in the central area B, $B^1$ and $B^2$ of the sleeve while providing a softer, more elastic support in these central areas in a longitudinal direction. Likewise, the end sections $A^1$, $C^1$, $A^2$ of the sleeves provide a stiffer elastic support for the joint and limb area along the axial direction of the sleeves as compared with the transverse direction. The sleeves will be sized to be somewhat smaller in a relaxed state than a limb area on which the sleeve is to be installed, and several size sleeves can be made to accommodate a wide range of limb sizes.

The use of a layer of silicone elastomer material on the interior surface of the sleeve enables the sleeve to fit snugly against the skin of the user in a very comfortable manner due to the ability of the silicone elastomer to absorb and react sheer loads between the skin and the fabric layer of the sleeve. The silicone elastomer material when in direct, airtight contact with the skin of the user holds back moisture in the skin of the user, thereby preventing perspiration or moisture to pass into the region between the skin of the user and the sleeve.

When the sleeve is used in a prosthetic application to provide an airtight seal between the residual limb of a user and the proximal end of a prosthetic socket, the silicone elastomer provides an airtight seal between the skin and the prosthetic socket while the elasticized fabric sections provide a comfortable interface between the residual limb and the socket. Again, the sleeve will be unrolled from a rolled up condition for donning on a residual limb and will be sized somewhat smaller than a residual limb and a prosthetic socket to ensure an airtight fit between the residual limb, the sleeve and the socket.

While only a pair of stiffening ribs 32, $32^1$ and $32^2$ have been illustrated, it will be understood that more than two such ribs may be utilized and that the ribs may be configured in different patterns to provide specific axial stiffness along certain directions of the orthotic or prosthetic sleeves described herein.

While a cured silicone elastomer material is described herein as the preferred interior covering material for the sleeves, other elastomeric or gel materials may be utilized to provide an interlayer between the fabric of the sleeve and the skin of a user.

The orthotic or prosthetic sleeve of the invention may be constructed by using other shapes or patterns of fabric other than those described herein, provided that they may be assembled together to form an orthotic or prosthetic sleeve wherein the elasticized fabric constituting the sleeve sections exhibit higher elastic stiffness along one direction of the fabric than along an orthogonal direction relative to the one direction. It would be possible, for example, to form sections A, B and C each from multiple fabric patterns sewn or otherwise connected together to form the individual sections.

The stiffening ribs 32, 32$^1$ and 32$^2$ also could be fabricated in the form of a pocket that could receive a separate stiffening element such as a plastic or metallic rod or band that would provide an enhanced stiffening function in and of themselves or in combination with the ribs.

It will be evident to those skilled in the art that the orthotic or prosthetic sleeve according to the invention can be constructed in different forms, shapes and configurations other than those specifically described herein without departing from the spirit and scope of the invention as defined in the appended claims.

What is claimed is:

1. An orthotic or prosthetic sleeve comprising:
   at least two elements formed of tubular shaped elasticized fabric connected together to define a tubular sleeve extending along an axis;
   the elasticized fabric constituting each of said elements having a higher elastic stiffness along one direction than along a direction that is orthogonal relative to the one direction;
   one of the at least two elements being formed so that the direction of higher elastic stiffness of the elasticized fabric forming said one element extends axially parallel with the sleeve axis and another of said at least two elements being formed so that the direction of higher stiffness of the elasticized fabric defining said other element extends generally transversely of the sleeve axis;
   wherein the interior surface of the sleeve is entirely coated with a continuous, cured silicone elastomer material, said silicone elastomer forming a discrete moisture and air impervious layer on the inside surface of the sleeve;
   wherein the silicone elastomer has a Shore OO of 25–70; a minimum tensile strength of 230 lbs/inch; a 100% modulus of 8 psi; a 500% modulus of 61 psi; a minimum tear strength of 49 lbs/inch; a maximum tensile strength of 500 lbs/inch; and an elongation of about 1000%.

2. An orthotic or prosthetic sleeve comprising:
   at least two elements formed of tubular shaped elasticized fabric connected together to define a tubular sleeve extending along an axis;
   the elasticized fabric constituting each of said elements having a higher elastic stiffness along one direction than along a direction that is orthogonal relative to the one direction;
   one of the at least two elements being formed so that the direction of higher elastic stiffness of the elasticized fabric forming said one element extends axially parallel with the sleeve axis and another of said at least two elements being formed so that the direction of higher stiffness of the elasticized fabric defining said other element extends generally transversely of the sleeve axis; and
   including at least one relatively inelastic, elongated, stiffening element continuously attached to the sleeve along an axial length of the outer surface of the sleeve.

3. An orthotic or prosthetic sleeve according to claim 2, wherein the stiffening element is a ribbon-like fabric sewn to the at least two elements.

4. An orthotic or prosthetic sleeve according to claim 3, wherein said at least one stiffening element comprises two stiffening elements extending axially along diametrically opposite sides of the at least two elements.

5. An orthotic or prosthetic sleeve comprising:
   at least three elements formed of tubular shaped elasticized fabric connected together to define a tubular sleeve extending along an axis;
   the elasticized fabric constituting each of said elements having a higher elastic stiffness along one direction than along a direction that is orthogonal relative to the one direction;
   said three fabric elements defining two end sections and a middle section between the end sections of said sleeve;
   said end sections being formed so that the direction of higher elastic stiffness of the fabric defining said end sections extends axially parallel with the sleeve axis and the middle section being formed so that the direction of higher elastic stiffness of the fabric defining said middle section extends generally transversely of the sleeve axis;
   wherein the interior surface of the sleeve is entirely coated with a continuous, cured silicone elastomer material, said silicone elastomer forming a discrete moisture and air impervious layer on the inside surface of the sleeve; and
   wherein the silicone elastomer has a Shore OO of 25–70; a minimum tensile strength of 230 lbs/inch; a 100% modulus of 8 psi; a 500% modulus of 61 psi; a minimum tear strength of 49 lbs/inch; a maximum tensile strength of 500 lbs/inch; and an elongation of about 1000%.

6. An orthotic or prosthetic sleeve comprising:
   at least three elements formed of tubular shaped elasticized fabric connected together to define a tubular sleeve extending along an axis;
   the elasticized fabric constituting each of said elements having a higher elastic stiffness along one direction than along a direction that is orthogonal relative to the one direction;
   said three fabric elements defining two end sections and a middle section between the end sections of said sleeve;
   said end sections being formed so that the direction of higher elastic stiffness of the fabric defining said end sections extends axially parallel with the sleeve axis and the middle section being formed so that the direction of higher elastic stiffness of the fabric defining said middle section extends generally transversely of the sleeve axis; and
   including at least one relatively inelastic, elongated, stiffening element continuously attached to the sleeve along an axial length of the outer surface of the sleeve.

* * * * *

UNITED STATES PATENT AND TRADEMARK OFFICE
CERTIFICATE OF CORRECTION

PATENT NO.         : 6,592,539 B1                                                   Page 1 of 1
APPLICATION NO.    : 09/516221
DATED              : July 15, 2003
INVENTOR(S)        : Palmi Einarsson et al.

It is certified that error appears in the above-identified patent and that said Letters Patent is hereby corrected as shown below:

ON THE TITLE PAGE

Item (73) Assignee should read: Ossur HF ~~Rujavik (GB)~~ <u>Reykjavik (IS)</u>

Signed and Sealed this

Eighteenth Day of May, 2010

David J. Kappos
*Director of the United States Patent and Trademark Office*